United States Patent [19]

Thym et al.

[11] Patent Number: 5,846,837
[45] Date of Patent: Dec. 8, 1998

[54] VOLUME-INDEPENDENT DIAGNOSTIC TEST CARRIER AND METHODS IN WHICH IT IS USED TO DETERMINE AN ANALYTE

[75] Inventors: Detlef Thym; Helmut Leininger, both of Mannheim, Germany

[73] Assignee: Boehringer Mannheim GmbH, Mannheim, Germany

[21] Appl. No.: 900,401

[22] Filed: Jul. 21, 1997

[30] Foreign Application Priority Data

Jul. 23, 1996 [DE] Germany ................. 196 29 657.9

[51] Int. Cl.$^6$ .................. G01N 33/52; G01N 33/49
[52] U.S. Cl. .................. 436/170; 436/177; 422/58; 422/56
[58] Field of Search ................. 436/63, 86, 169, 436/170, 177, 178; 422/56, 58, 61, 100–104

[56] References Cited

U.S. PATENT DOCUMENTS

| | | | |
|---|---|---|---|
| 2,785,057 | 3/1957 | Schwab et al. | 422/58 |
| 3,509,872 | 5/1970 | Truhan | 422/58 |
| 3,802,842 | 4/1974 | Lange et al. | 422/56 |
| 4,258,001 | 3/1981 | Pierce et al. | 422/56 |
| 4,312,834 | 1/1982 | Vogel et al. | 422/56 |
| 4,477,575 | 10/1984 | Vogel et al. | 436/170 |
| 4,647,430 | 3/1987 | Zweig | 422/58 |
| 4,816,224 | 3/1989 | Vogel et al. | 422/58 |
| 5,096,836 | 3/1992 | Macho et al. | 436/169 |
| 5,536,470 | 7/1996 | Frey et al. | 422/56 |

FOREIGN PATENT DOCUMENTS 15879   2/1992   WIPO .

OTHER PUBLICATIONS

International Publication No. WO 92/15879 published Sep. 17, 1992 Abstract only.

Primary Examiner—Lyle A. Alexander
Attorney, Agent, or Firm—Nikaido, Marmelstein, Murray & Oram LLP

[57] ABSTRACT

The present invention concerns a diagnostic test carrier (1) containing a supporting layer (2) with a detection layer (3) arranged thereon containing the reagents required to determine analyte in a liquid sample and a network (4) covering the detection layer (3) which is larger than the detection layer (3) and which is attached to the supporting layer (2), which is characterized in that the network (4) is hydrophilic but not capillary active on its own and an inert cover (5) made of sample-impermeable material is arranged over the areas (6) of the network that extend beyond the detection layer in such a way that a sample application site (7) remains free on the region of the network (4) covering the detection layer as well as the use of such a test carrier for the determination of analyte in a liquid. In addition the invention concerns a method for the determination of an analyte in a liquid sample with the aid of a test carrier according to the invention.

40 Claims, 11 Drawing Sheets

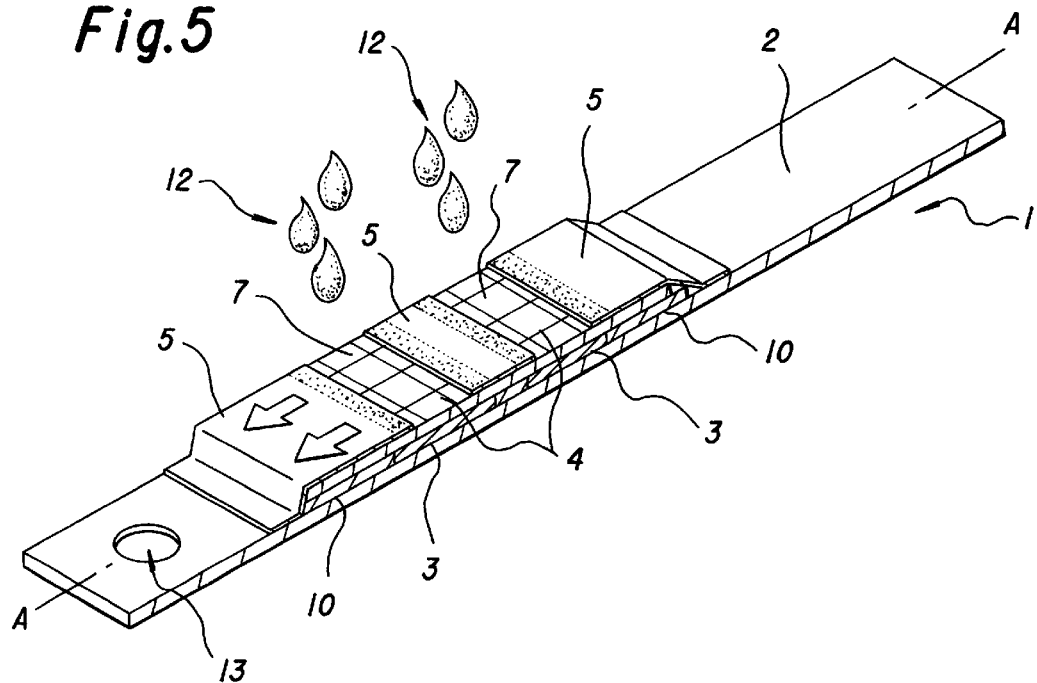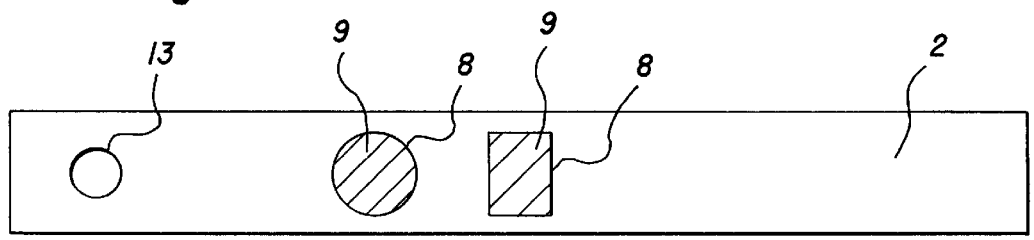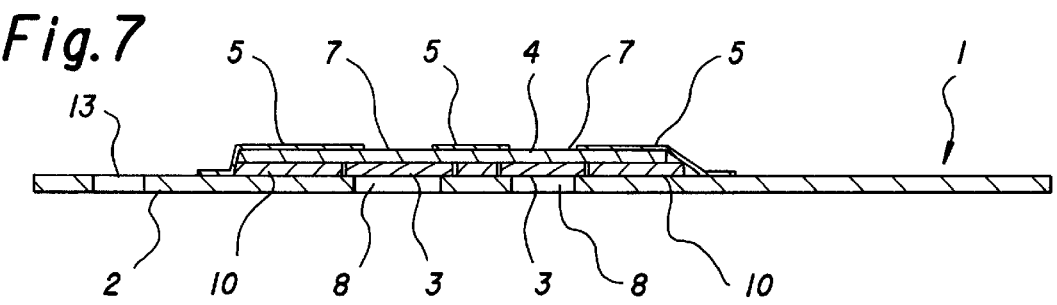

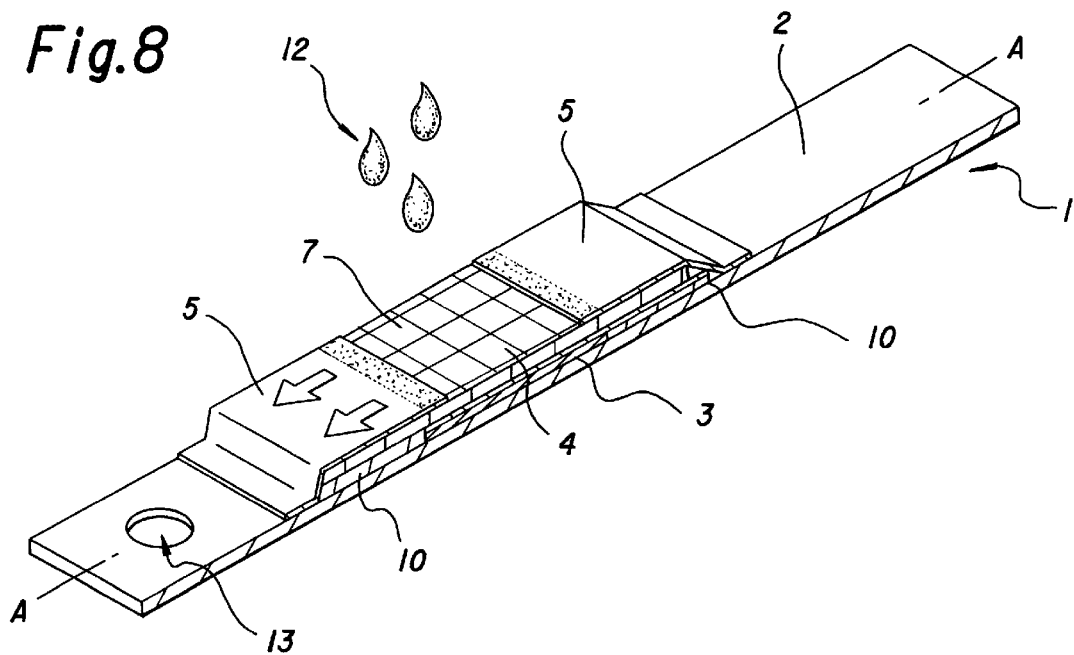
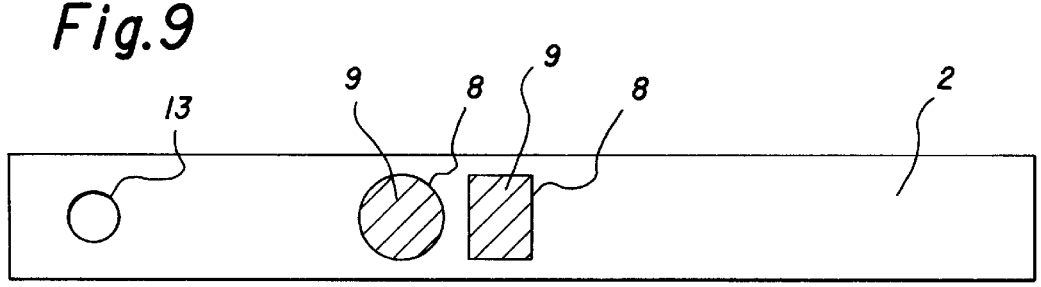
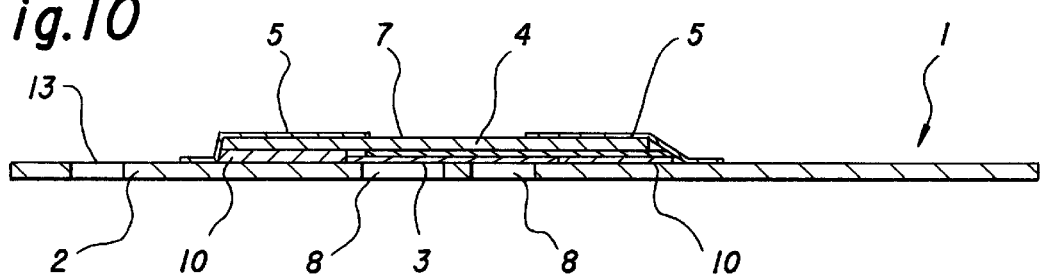

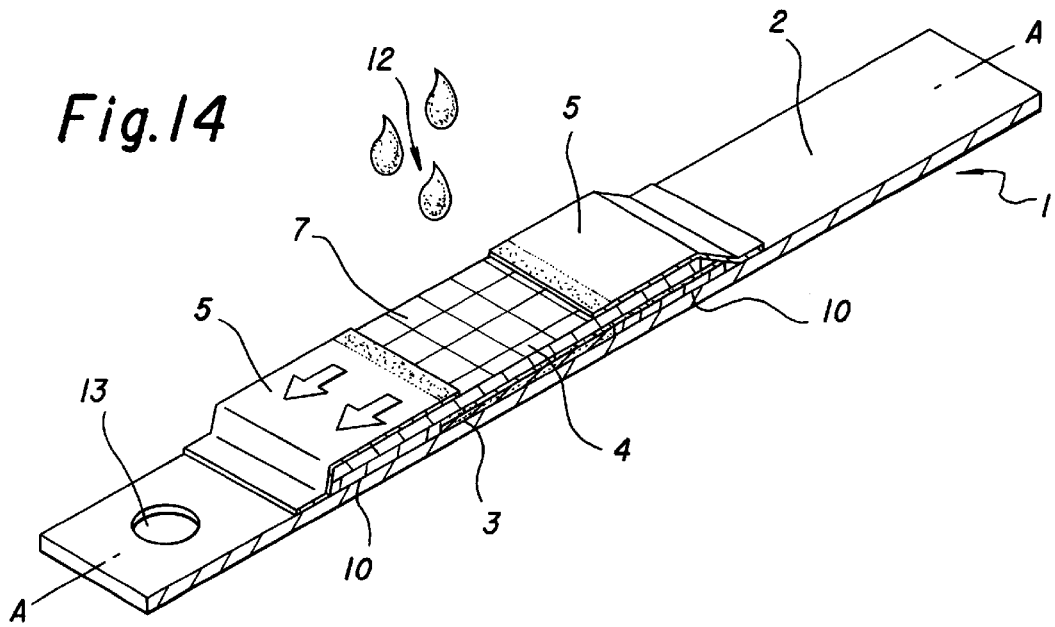
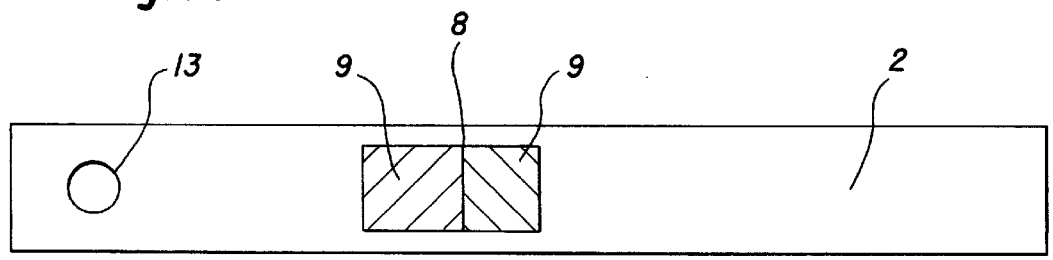
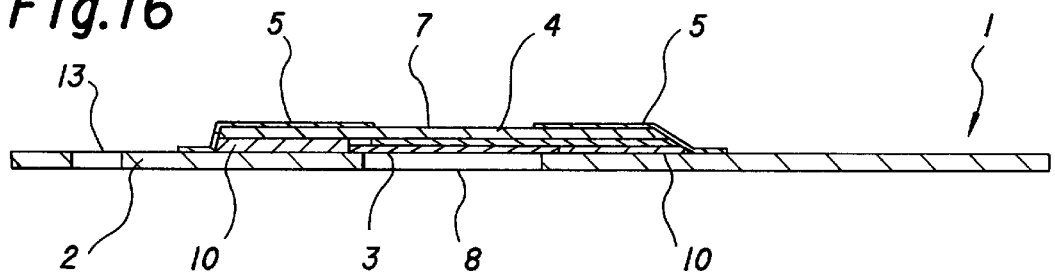

VOLUME-INDEPENDENT DIAGNOSTIC TEST CARRIER AND METHODS IN WHICH IT IS USED TO DETERMINE AN ANALYTE

The invention concerns a diagnostic test carrier containing a supporting layer with one or several detection layers arranged thereon containing reagents necessary to determine an analyte in a liquid sample and a network covering the detection layers which is larger than the detection layers and which is attached to the supporting layer. In addition the invention concerns the use of this diagnostic test carrier for the determination of an analyte in a liquid and a method for the determination of an analyte in a liquid sample with the aid of a diagnostic test carrier according to the invention.

So-called carrier-bound tests are often used for the qualitative or quantitative analytical determination of components of body fluids in particular of blood. In these the reagents are present on or in appropriate layers of a solid test carrier which is contacted with the sample. The reaction of the liquid sample and reagents leads to a detectable signal in particular to a change in colour which can be analyzed visually or with the aid of an instrument, usually by reflection photometry.

Test carriers are frequently in the form of test strips which are composed essentially of an elongated supporting layer made of plastic material and detection layers as test zones mounted thereon. However, test carriers are also known which are shaped as small quadrangular or rectangular plates.

Test carriers of the type referred to above are known for example from the German Patent document 21 18 455. In this document diagnostic carriers for the detection of analytes in liquids are described which are composed of a supporting layer and at least one detection layer containing the detection reagents whose surface which does not rest against the supporting layer is provided with a covering layer. The covering layer can be composed of a fine-meshed network in the form of a fabric, knitted fabric or fleece. Plastic fabrics are stated as being preferred networks in order to achieve a rapid wetting of the detection layer with sample liquid and to avoid interfering chromatographic effects. In order to detect an analyte in a liquid such a diagnostic test carrier is immersed in a corresponding liquid preferably urine. The detection layer thus comes into contact with a very large excess of fluid which cannot be taken up by the test carrier. However, depending on the duration of contact of the detection layer with the liquid to be examined, different colour intensities are observed. As a rule longer contact times lead to more positive results. Hence a correct quantitative analyte determination is not possible in this manner.

A frequent cause of false measured values in diabetes monitoring, i.e. the regular control of the blood of diabetics for glucose content, is on the one hand an inadequate sample volume. Test carriers with the smallest possible volume requirement are therefore the object of a variety of current developments. However, such test carriers must not only yield correct measured values with very small sample volumes of about 3 $\mu$l, but they must also work reliably with relatively large sample volumes of about 15–20 $\mu$l and must retain the sample liquid. If liquid leaks out of the test carrier then hygienic problems may occur, for example if potentially infectious foreign blood is measured or if it is intended to measure the test carrier by an apparatus and there is then a danger of contaminating the instrument. To the knowledge of the patent applicant this goal has up to now still not yet been achieved in a simple and satisfactory manner.

Therefore the object of the present invention is to provide a diagnostic test carrier for the quantitative determination of analyte in a liquid on which an undosed amount of sample liquid can be applied. Sample volumes above 3 $\mu$l should be adequate. However, an excess of sample liquid should not lead to time-dependent false positive results. Furthermore excess sample liquid should not cause hygienic problems and the test carrier should be as simple as possible to manufacture.

This object is achieved by the invention characterized in more detail in the patent claims.

The subject matter of the invention is namely a diagnostic test carrier with a supporting layer and a detection layer arranged thereon which contains the reagents required to determine analyte in a liquid sample. The detection layer is covered by a network which is larger than the detection layer and which is fastened onto the supporting layer outside the detection layer. The network of the diagnostic test carrier according to the invention is hydrophilic but alone it is not capillary active. An inert cover made of material that is impermeable to sample liquid is arranged over those areas of the network which extend beyond the detection layers in such a way that an area remains free for sample application in the region of the network which is located above a detection layer.

The invention in addition concerns the use of such a diagnostic test carrier to determine analyte in a liquid. Hence a method for the determination of analyte in a liquid sample with the aid of such a diagnostic test carrier is also a subject matter of the invention in which the sample liquid is applied to the sample application site. The network leads excess liquid from the detection layer into the region of the network which extends beyond the detection layer whereupon the detection layer can then be observed for signal generation. The signal generation is a measure of the presence or the amount of analyte in the sample to be examined.

The network of the diagnostic test carrier according to the invention should itself not be capillary active or absorptive so that the sample liquid is available as completely as possible for the detection layer. Those networks have proven to be suitable which enable water to rise in the network by less than 2 mm when it is immersed vertically in water. Coarse-meshed monofilament fabrics which are hydrophilic are preferably used as the network. For this the fabric material can itself be hydrophilic or it can be made hydrophilic by for example treatment with a wetting agent. Polyester is particularly preferably used as a net material in which case the net made out of this material is then used after treatment with wetting agents.

The thickness of the network must be such that the cover which rests on it and the layer below it are at such a distance from one another that remaining liquid is sucked over the saturated detection layer and into the filled meshes of the network by capillary force in the area under the cover and is led away from the sample application site. As a rule a network thickness of 50 to 400 $\mu$m is advantageous for this.

The net must have an adequately large mesh width so that liquid can pass through the net onto the detection layer. The nature of the network is such that liquid is not spread horizontally in the net over the net surface but it flows vertically through the net onto the detection layer.

In a diagnostic test carrier according to the invention materials which come into particular consideration for the supporting layer are those which do not take up the liquids to be examined. These are so-called non-absorptive materials, plastic foils made for example of polystyrene, polyvinyl chloride, polyester, polycarbonate or polyamide being particularly preferred. However, it is also possible to impregnate absorptive materials such as wood, paper or cardboard with water-repellent agents or to coat them with a water-resistant film in which case silicones or hard fats can be used as hydrophobing agents and for example nitrocellulose or cellulose acetate can be used as film formers. Metal foils or glass are also suitable as further supporting materials.

In contrast for a detection layer it is necessary to use materials which are able to take up the liquid to be examined together with the components contained therein. These are so-called absorptive materials such as fleeces, fabrics, knitted fabrics, membranes or other porous plastic materials or swellable materials such as gelatin or dispersion films which can be used as layer materials. The materials which come into consideration for the detection layer must of course also be able to carry the reagents that are necessary for the detection of the analyte to be determined. In the simplest case all reagents required for the analyte test are on or in a layer. However, cases are also conceivable for which it is more advantageous to divide the reagents among several absorptive or swellable material layers which are then arranged on top of one another with their whole faces in contact. The term "detection layer" used in the following is intended to encompass those cases in which the reagents are located either only in or on one layer or in two or even more layers arranged as described above.

In addition the detection layer can also contain a layer which is able to separate plasma or serum from whole blood such as for example a glass fibre fleece as is known for example from EP-B-0 045 476. One or several such separating layers can lie on top of one or several layers which carry detection reagents. Such a structure is also intended to be included by the term "detection layer".

Preferred materials for the detection layer are papers or porous plastic materials such as membranes. Of these asymmetric porous membranes are particularly preferred which are arranged advantageously such that the sample liquid to be examined is applied to the large-pored side of the membrane and the analyte is determined from the fine-pored side of the membrane. Polyamide, polyvinylidene difluoride, poylethersulfone or polysulfone membranes are quite especially preferred as porous membrane materials. Polyamide 66 membranes and hydrophilized asymmetric polysulfone membranes are in particular excellently suitable. The reagents for the determination of the analyte to be detected are usually introduced by impregnation into the aforementioned materials or are applied to one side by coating. When coating asymmetric membranes the fine-pored side is advantageously coated.

However, so-called open films also come into consideration for the detection layer as described for example in EP-B-0 016 387. For this an aqueous dispersion of film-forming organic plastic solids are added as fine insoluble organic or inorganic particles and the reagents required for the detection reaction are additionally added. Suitable film formers are preferably organic plastics such as polyvinyl esters, polyvinyl acetates, polyacrylic esters, polymethacrylic acid, polyacrylamides, polyamides, polystyrene, mixed polymers such as of butadiene and styrene or of maleic acid esters and vinyl acetate or other film forming natural and synthetic organic polymers as well as mixtures of the same in the form of aqueous dispersions. The dispersions can be painted onto a base to form a uniform layer which yields a water-resistant film after drying. The dry films have a thickness of 10 $\mu$m to 500 $\mu$m preferably of 30 to 200 $\mu$m. The film can be used with the base together as a carrier or can be mounted on another carrier for the detection reaction. Although the reagents required for the detection reaction are normally added to the dispersion used to produce the open films, it may also be advantageous to impregnate the film that is formed with the reagents after it has been manufactured. It is also possible to pre-impregnate the fillers with the reagents. Which reagents can be used to determine a particular analyte is known to a person skilled in the art. This does not need to be elucidated here in more detail.

A further example of a preferred detection layer according to the invention is a film layer as described in WO-A-92 15 879. This layer is produced from a dispersion of the emulsion of a polymeric film former which additionally contains a pigment, a swelling agent and a detection reagent in a homogeneous dispersion. Polyvinyl esters, polyvinyl acetates, polyacrylic esters, polymethacrylic acid, polyvinyl amides, polyamides and polystyrene are especially suitable as polymeric film formers. In addition to homopolymers mixed polymerizates are also suitable such as of butadiene, styrene or maleic acid ester. Titanium dioxide is a particularly suitable pigment for the film. The swelling agent used should have particularly good swelling properties, methyl vinyl ether maleic acid anhydride copolymers being particularly recommended. It is left to a person skilled in the art which reagents are used to determine a particular analyte.

In a diagnostic test carrier according to the invention it is quite especially preferred to use a test field as a detection layer which is composed of two layers. This test field comprises a transparent foil on which a first and a second film layer are mounted on top of one another in this order. It is important that the first layer located on the transparent foil scatters light considerably less in a wet state than the overlying second layer. The non-coated side of the transparent foil is referred to as the detection side and the side of the second layer which is opposite to the side with which the second layer rests on the first is referred to as the sample application side.

The film layers are produced from dispersions or emulsions of polymeric film formers. Dispersion film formers contain microscopic polymer particles which are insoluble in the carrier liquid (usually water) and are finely dispersed in the carrier liquid. If the liquid is removed by evaporation during film formation then the particles come closer and finely touch one another. The large forces which occur in this process and the gain in surface energy which accompanies the film formation results in the particles growing into a substantially closed film layer. Alternatively it is also possible to use an emulsion of the film former in which this is dissolved in a solvent. The dissolved polymer is emulsified in a carrier liquid which is immiscible with the solvent.

Polyvinyl esters, polyvinyl acetates, polyacrylic esters, polymethacrylic acid, polyvinyl amides, polyamides and polystyrene are particularly suitable as polymers for such film formers. In addition to homopolymers mixed polymerizates are also suitable such as of butadiene, styrene or maleic acid ester.

The two so-called film layers are located on a transparent foil in the test field. For this those plastic foils come into consideration which are impermeable to liquid. Polycarbonate foil has proven to be particularly suitable.

The two film layers can be produced from coating compounds which contain the same polymeric film formers or they can be produced from coating compounds which contain different polymeric film formers. Whereas the first layer contains a swelling agent and optionally a weakly light scattering filler, the second layer requires a swelling agent and in any case at least one pigment that scatters light strongly. In addition the second layer can also contain non-porous fillers as well as porous fillers such as kieselguhr in small amounts without becoming permeable for erythrocytes.

By adding a swelling agent that swells well (i.e. a substance which increases its volume when it takes up water) one does not only obtain layers which can be penetrated relatively rapidly by sample liquid but have good erythrocyte and additionally also blood pigment separation properties despite this opening effect of the swelling agent. The swelling properties should be so good that for a test in which the rate of colour formation—such as for example of a glucose test reaction—is mainly dependent on the penetration of the sample liquid through the layer, the optically detectable reaction is measurable after a maximum of one minute. Especially suitable swelling agents have proven to be methyl vinyl ether maleic acid anhydride copolymer, xanthan gum and methyl vinyl ether maleic acid copolymer.

Kieselguhr is also denoted diatomaceous earth. These are deposits that have formed from silicic acid backbones of the diatomaceous types which are mined in various places. The kieselguhr that is preferably used has an average particle diameter of 5–15 μm, these values being determined with a type 715 laser granulometer which is sold by the Pabisch Company, Munich, Germany.

The amount of the strongly light-scattering pigment in the second layer is at least 25% by weight relative to the dry ready-to-use double layer of the test field. Since the weakly light-scattering fillers and the strongly light-scattering pigments are essential for the optical properties of the film layers, the first and the second film layer have different fillers and pigments.

The first film layer should either contain no fillers or those fillers whose refractive index is near to the refractive index of water. Silicone dioxide, silicates and aluminium silicates have proven to be particularly suitable for this. A sodium aluminium silicate with the commercial name Traspafill® is particularly preferred.

According to the invention the second layer should scatter light very strongly. Ideally the refractive index of the pigments in the second film layer should be at least 2.5. Hence titanium dioxide is preferably used. Particles with an average diameter of 0.2 to 0.8 μm have proven to be particularly advantageous. Easily processable titanium dioxide types in the anatase modification are quite especially preferred.

Reagent systems for the detection of particular analytes by colour formation are known to a person skilled in the art. It is possible that all components of the reagent system are located in one film layer. However, it is also possible that the components of the reagent system are divided among two film layers. The colour generating reagent system is advantageously located at least partially in the first film layer.

Colour formation within the scope of the present invention is not only understood as a transition from white to coloured but also as any change in colour, such changes of colour of course being particularly preferred which are associated with the largest possible shift of the maximum absorption wavelength ($\lambda_{max}$)

In order to optimize the test field in the diagnostic test carrier according to the invention it has proven to be particularly advantageous when both film layers do not contain a haemolyzing netting agent. Neutral i.e. non-charged netting agents are particularly preferred for this. N-octanoyl-N-methyl glucamide is most particularly preferred.

In order to produce a test field of a diagnostic test carrier according to the invention the respective film layers are each produced successively from a homogeneous dispersion of the said components. For this the transparent foil is used as a base to form the coating compound for the first film layer. After the coating compound for the first film layer has been applied with a particular layer thickness, the layer is dried. Afterwards the coating compound for the second layer is applied to this layer also with a thin layer thickness and dried. After the drying the thickness of the first and second film layer should be together no more than 0.2 mm, preferably no more than 0.12 mm particularly preferably no more than 0.08 mm. The dry second film layer is preferably about 2 to 5-times thicker than the first.

The test carrier according to the invention can have one detection layer. It can, however, also contain several detection layers arranged next to one another. In the case of several detection layers these can be the same or different so that one and the same analyte can be determined in parallel in several detection layers or different analytes can be detected in each case in another detection layer. However, it is also possible that several spatially separate reaction zones are located next to one another on one detection layer so that in this case also either the same analyte can be detected several times or different analytes can be detected in parallel in the same detection layer. In the latter case the material of the layer is the same apart from the reagents for the determination of the analyte. Different reagents are located in different reaction zones. Different reaction zones can be present side by side and touching one another or they can be separated by intervening areas which do not form a signal with the analyte.

In the diagnostic test carrier according to the invention the network which covers the detection layer is larger than the underlying detection layer. The part of the network which extends beyond the detection layer i.e. that part of the network which is not in contact with the detection layer is fixed directly or indirectly via spacers to the supporting layer outside the detection layer. The attachment can be achieved by methods known to a person skilled in the area of test carrier technology. For example it can be attached by hot-setting adhesive or hardening cold-setting adhesive. In this case a point or patterned glueing is advantageous since capillary active liquid transport can take place particularly well in this case. Double-sided adhesive strips have also proven advantageous. However, in all cases it is important that the attachment of the network to the supporting layer is such that a capillary active liquid transport is possible from the detection layer into that part of the network which is attached to the supporting layer. This capillary active liquid transport must in particular be possible when the detection layer is saturated with liquid. Adhesive tapes made of natural or synthetic rubber have proven to be particularly suitable for the processing. It is quite especially advantageous when the agent that serves to attach the network to the supporting layer has about the same thickness as the detection layer(s). It then serves more or less as a spacer in order to hold the network overall in a continuous plane also outside the area of the detection layer(s).

If the diagnostic test carrier according to the invention contains several detection layers next to one another then a network can cover all detection layers or several networks can be used.

In order to determine the analyte to be detected in the sample liquid, the detection layer and at least the reaction zones i.e. the areas of the detection layer(s) carrying reagent which can be observed and measured with regard to signal formation are visible through the supporting layer in the diagnostic test carrier according to the invention. This can be achieved by a transparent supporting layer. However, it is also possible that the supporting layer has a perforation which is covered by the detection layer or the detection layers. The detection layer or the detection layers and at least the reaction zones of the detection layers are then visible through the perforation. In a preferred embodiment of the diagnostic test carrier according to the invention there is a hole in the supporting layer below a detection layer through which the detection layer or a reaction zone can be observed. The hole has a somewhat smaller diameter than the smallest linear dimension of the detection layer so that the detection layer outside the hole lies on the supporting layer and can be attached there. Double-sided adhesive strips located next to both sides of the detection layer advantageously fix it to the network lying over the detection layer and it is adequately attached to the supporting layer. However, the detection layer itself is also preferably attached to the supporting layer by means of a thin adhesive tape.

However, several reaction zones of a detection layer may also be visible through one hole.

The perforation of a diagnostic test carrier according to the invention can be composed of two or several holes which can be used to determine analyte (one or several analytes). Various detection layers can be arranged over the holes or only one detection layer with several reaction zones so that one detection layer or one reaction zone can be observed through one hole in each case. It is also possible that several reaction zones can be observed through one hole.

An inert cover made of sample-impermeable, as a rule water-impermeable and non-absorptive material is placed over the network of the diagnostic test carrier of the invention in such a way that the region of the network outside the detection layer is covered. Ideally the cover also protrudes a little beyond the region of the detection layer. However, in any case a considerable part of the network that covers the detection layer remains free. This free part of the network is denoted sample application site.

Plastic foils have proven to be particularly advantageous as a cover. If the cover and network have different colours for example white and yellow or white and red it is possible in this way to mark the site very well where the sample liquid to be examined should be applied.

With for example one or several printed arrows on the cover it can be also made clear in which direction i.e. with which end a diagnostic test carrier according to the invention should be placed or inserted into a measuring instrument.

A sample application site can be achieved particularly simply by a cover with the aid of two tape-like plastic foils which leave a tape-like zone of the network that covers the detection layer free. If two or several sample application sites are provided, three or more tape-like plastic foils have to be used. The foils used to cover are attached to the network and optionally to the supporting layer. Hot melt adhesives which are for example applied as dots or as a raster to the supporting layer or to the underside of the cover are suitable for such an attachment or adhesive tapes if the foils are not themselves adhesive. However, in any case care must be taken that a capillary gap formed by the network remains under the cover in which excess sample liquid can be taken up from a detection layer saturated with liquid. The sample application site is preferably above the perforation in the supporting layer through which signal formation can be observed in the detection layer.

In order to carry out a method for the determination of analyte in a liquid sample with the aid of a diagnostic test carrier according to the invention, sample liquid is applied to the side of the network which faces away from the detection layer, ideally so much that the liquid passing through the network completely saturates the detection layer. Body fluids such as blood, plasma, serum, urine, saliva etc. come into particular consideration as the sample liquid. Blood or liquids derived from blood such as plasma or serum as well as urine are particularly preferred sample liquids. Excess liquid is led away by the network from the detection layer into the region of the network which extends beyond the detection layer. Then a signal can be detected in the detection layer when the analyte to be determined is present. Such a signal is preferably a change in colour which is understood as a colour generation, loss of colour as well as colour transition. The intensity of the colour change is a measure of the amount of analyte in the examined liquid sample. It can be evaluated visually or quantitatively with the aid of an instrument, usually by reflection photometry.

If too little liquid reaches the detection layer, i.e. less than is necessary to saturate the layer, regions of the detection layer remain dry which can be seen from above and below because liquid can only reach the detection layer vertically through the network and there is no horizontal spreading of liquid over the surface of the network. Since if the analyte is present a signal is generated only in the thoroughly moistened region of the detection layer, an inhomogeneous signal generation can be seen visually or by an instrument through the network as well as through the supporting layer. This is a clear indication for the person carrying out the examination that too little sample liquid has been used and hence the result of the examination may be false. Even if no analyte is present in the sample, visual or reflectometric measurement of several partial regions of the detection layer can for example establish that only a part of the detection layer is moistened and thus too little sample liquid had been applied.

In addition to marking the sample application site, such a cover also supports the capillary forces which conduct excess liquid away from the detection layer. In addition the cover also protects the excess liquid conducted away from the detection layer from external contact and prevents such liquid from easily dripping from the test carrier.

A major advantage of the diagnostic test carrier according to the invention is that it is not necessary to apply a predetermined volume of a sample liquid to the test carrier. Excess liquid is conducted away from the detection layer as already mentioned by the network protruding beyond the detection layer. Since excess liquid is conducted away from the detection layer, hygienic aspects are also taken into consideration. A dripping of liquid from the test carrier or contact of liquid for example with parts of an instrument into which the test carrier is placed for instrumental evaluation is reliably avoided. This is a very important aspect in the examination of blood or samples derived from blood such as plasma or serum.

The size of the region of the network that extends beyond the detection layer (the part of the network extending beyond the detection layer) depends on the largest sample volume expected in practice so that liquid that is really excess can also be conducted away from the detection layer. In this manner the signal intensity which occurs when an analyte is present is independent of the amount and the duration of contact of the sample liquid with the detection layer. The colour which is formed after completion of the detection reaction, usually within a few seconds until a few minutes, thus remains unchanged for the measurement. It is merely determined by the stability of the colour generating system but not for example by analyte which diffuses back from the excess liquid into the detection layer. False positive results are also avoided and a quantitative analyte determination becomes possible.

The covering of parts of the network and thus the marking of the sample application site ensures that liquid can only be placed on the optimal site for it on the detection layer. In combination with a detection layer which only takes up a small amount of liquid and nevertheless ensures an intensive signal generation, it is ensured that reliable analyte determinations are possible even with very small sample volumes. It can be manufactured very cheaply due to the fact that the test carrier according to the invention is only composed of only a few components which can be assembled simply and rapidly.

Preferred embodiments of the diagnostic test carrier according to the invention are shown in FIGS. 1–23.

BRIEF DESCRIPTION OF THE DRAWINGS

FIG. 5 shows a perspective view of a diagnostic test carrier according to the invention with two sample application sites.

FIG. 6 shows a top view of the underside of a diagnostic test carrier of FIG. 5 according to the invention with a perforation comprising a round and rectangular hole under two separated detection layers.

FIG. 7 shows a cross-section along A—A through a diagnostic test carrier of FIG. 5 according to the invention.

FIG. 8 shows a perspective view of a diagnostic test carrier according to the invention with an extra large sample application site.

FIG. 9 shows a top view of the underside of a diagnostic test carrier of FIG. 8 according to the invention with a perforation comprising a round and rectangular hole under an extra large detection layer.

FIG. 10 shows a cross-section along A—A through a diagnostic test carrier of FIG. 8 according to the invention.

FIG. 14 shows a perspective view of a diagnostic test carrier according to the invention with an extra large sample application site.

FIG. 15 shows a top view of the underside of a diagnostic test carrier of FIG. 14 according to the invention with a perforation comprising an extra large rectangular hole under a detection layer with two adjoining reaction zones.

FIG. 16 shows a cross-section along A—A through a diagnostic test carrier of FIG. 14 according to the invention.

Figure 1:
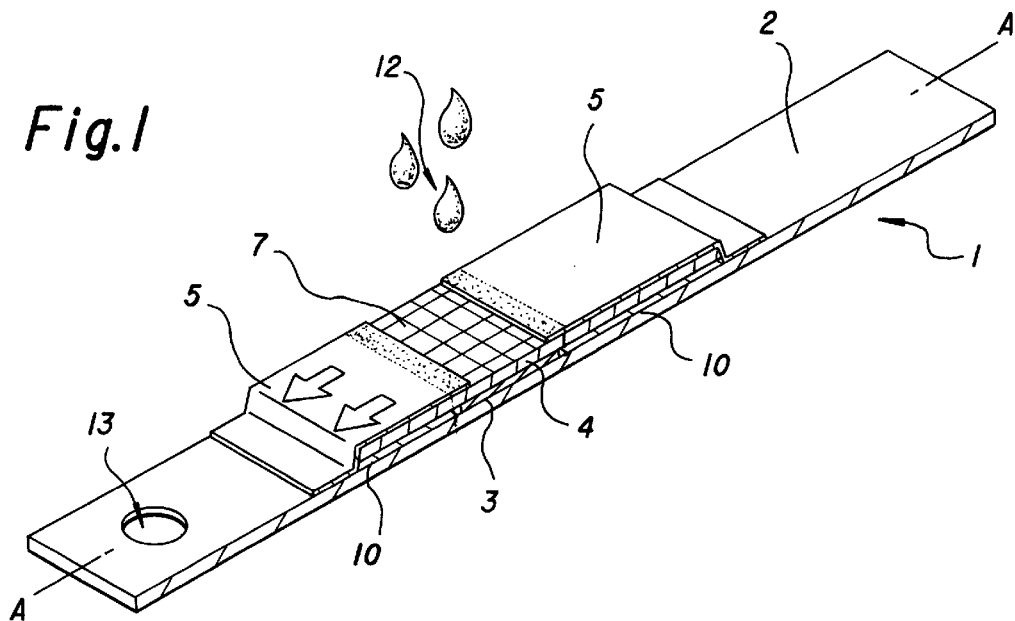
FIG. 1 shows a perspective view of a diagnostic test carrier according to the invention with a sample application site.

The reference numerals used in the Figures have the following meanings.

| | |
|---|---|
| 1 | diagnostic test carrier |
| 2 | supporting layer |
| 3 | detection layer |
| 4 | network |
| 5 | cover |
| 6 | region of the network that extends beyond the detection layer |
| 7 | sample application site |
| 8 | perforation |
| 9 | reaction zone |
| 10 | spacer |
| 11 | capillary active gap |
| 12 | sample liquid |
| 13 | positioning hole |
| 14 | adhesive tape attachment for the detection layer |

Figure 3:
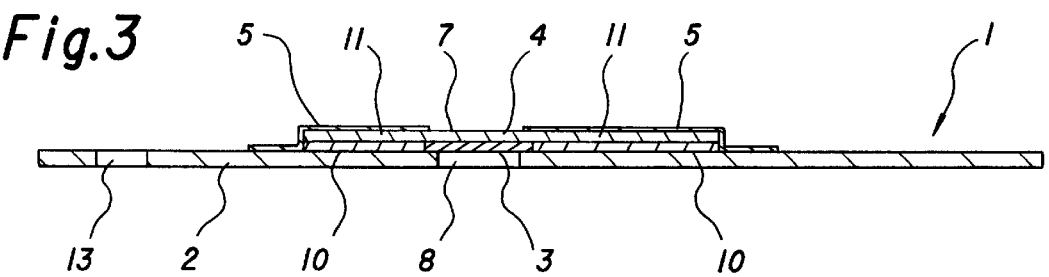
FIG. 3 shows a cross-section along A-A through a diagnostic test carrier according to the invention according to FIG. 1.

The diagnostic test carrier (1) according to the invention shown in perspective in FIG. 1 and in cross-section in FIG. 3 is in the form of a test strip. On a supporting layer (2) there are located a detection layer (3) which is covered by a larger network (4). The network (4) is attached to the supporting layer (2) next to the detection layer (3) by means of spacers (10). These spacers can be hot-melt adhesive areas or double-sided adhesive tapes which fix the network (4) onto the supporting layer (2). Ideally the spacers (10) have approximately the same thickness as the detection layer (3). The layers serving as a cover(s) are attached to the supporting layer (2) and the network (4). They are arranged such that they cover the region of the network (4) which extends beyond the detection layer (3). The covers (5) also extend slightly beyond the detection layer (3). However, they leave most of that part of the network (4) free which covers the detection layer (3). This area represents the sample application site (7). The sample liquid (12) to be examined is applied to this area. The positioning hole (13) enables the test strip to be held at an exact predetermined position of the apparatus in the case of measurement by an apparatus such as by reflection photometry. This can for example be achieved by a pin which extends into the positioning hole (13) and thus holds the test carrier (1) at a predetermined position. The left cover (5) contains printed arrows which show the user which end of the test carrier (1) should be placed or inserted into a measuring instrument.

Figure 2:
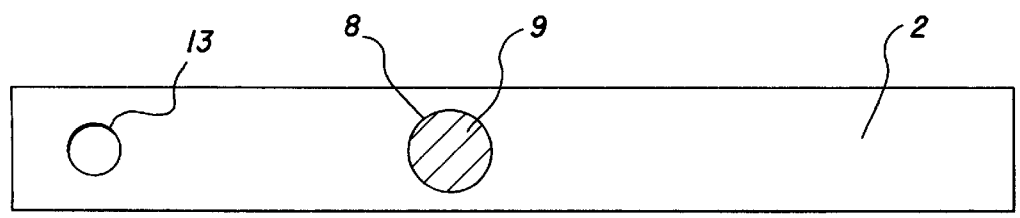
FIG. 2 shows a top-view of the underside of a diagnostic test carrier of FIG. 1 according to the invention with a round perforation under the detection layer.
Figure 4:
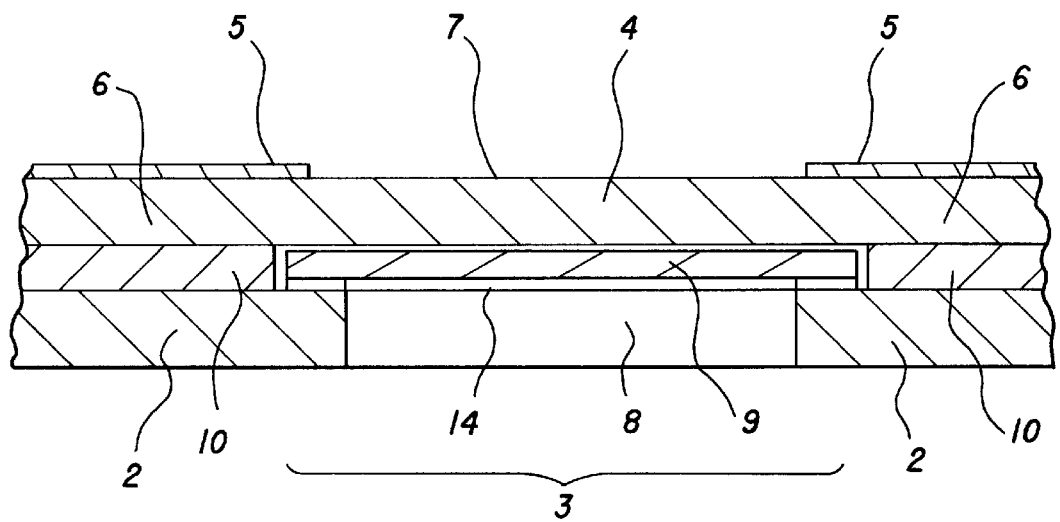
FIG. 4 shows an enlargement of a part of the cross-section of FIG. 3.

FIG. 4 shows an enlarged cross-section through a diagnostic test carrier according to the invention as shown in FIGS. 1 and 3. This Figure is intended to elucidate how a method for the determination of an analyte in a liquid sample proceeds. For such a determination sample liquid is applied to the sample application site (7) of the network (4). The liquid penetrates vertically through the network (4) into the detection layer (3) which in turn is attached with double-sided adhesive tape (14) to the supporting layer (2). The adhesive tape attachment (14) contains a hole which corresponds to the perforation (8) of the supporting layer (2) and which also lies exactly over this perforation (8). If sufficient sample liquid has been applied, this liquid disperses in the detection layer (3) over the entire reaction zone (9). If the liquid volume is very small the detection layer (3) may even suck dry the overlying network (4) since the network (4) is not itself capillary active. In the case of medium to large liquid volumes the void spaces of the network (4) over the detection layer (3) fill first and subsequently the capillary voids under the covers (5). For these capillary voids to function properly it is necessary that the covers (5) overlap at least slightly the area of the detection layer (3) under the network (4). The reaction zone (9) of the detection layer (3) can be observed through the perforation (8). For this aspect a top view of the underside of the diagnostic test carrier according to FIG. 1, 3 and 4 is shown in FIG. 2. If analyte is present in the applied sample liquid, the reaction zone (9) will change. A signal forms, for example a colour change, the intensity of which is a measure of the amount of analyte in the sample liquid.

The diagnostic test carrier according to the invention shown in FIG. 5 to 7 is one with two detection layers (3) which are accessible for sample liquid (12) via two sample application sites (7) that are located above them. The sample application sites (7) are formed by three strip-like covers (5) which cover the areas of the network which extend beyond the detection layers (3). In the example shown a continuous network (4) has been used. However, it is also possible to use two separate networks (4) with an intervening liquid barrier such as for example an adhesive tape or a strip of hot-melting adhesive. A perforation (8) is located in the supporting layer (2) of the test carrier (1) comprising two holes which each enable one reaction zone (9) of one of the two detection layers (3) to be observed. Such a test carrier (1) is for example suitable for the simultaneous determination of two different analytes. In this case the spatial separation of the detection layers (3) is advantageous if the reagents or the reaction products can interfere with each other.

The diagnostic test carrier (1) of FIGS. 8 to 10 according to the invention has an extra large sample application site (7) over a detection layer (3) which can be observed through a perforation (8) comprising two holes. Different reaction zones (9) can for example be arranged above the two holes which contain reagents for different analytes. Hence two analytes can be determined from one sample. The two reaction zones can, however, also be used to determine the same analyte with different sensitivities.

Figure 11:
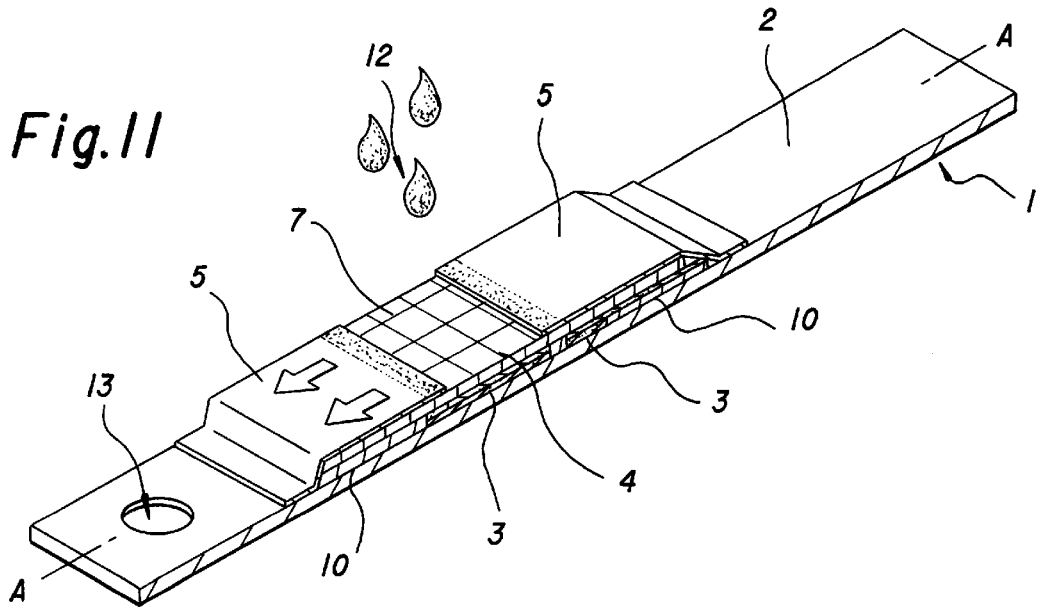
FIG. 11 shows a perspective view of a diagnostic test carrier according to the invention with a sample application site over one of two detection layers.
Figure 12:
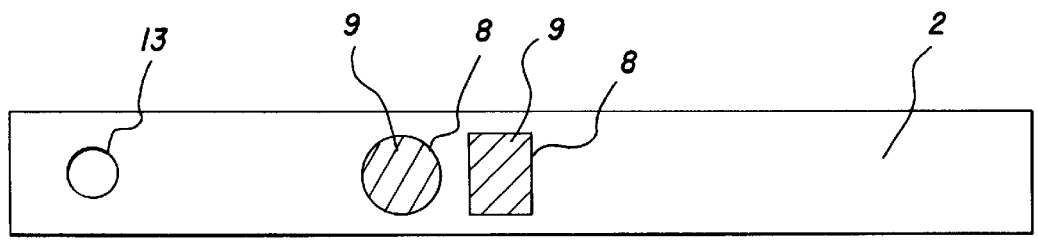
FIG. 12 shows a top view of the underside of a diagnostic test carrier of FIG. 11 according to the invention with a perforation comprising a round and rectangular hole under two separate detection layers.
Figure 13:
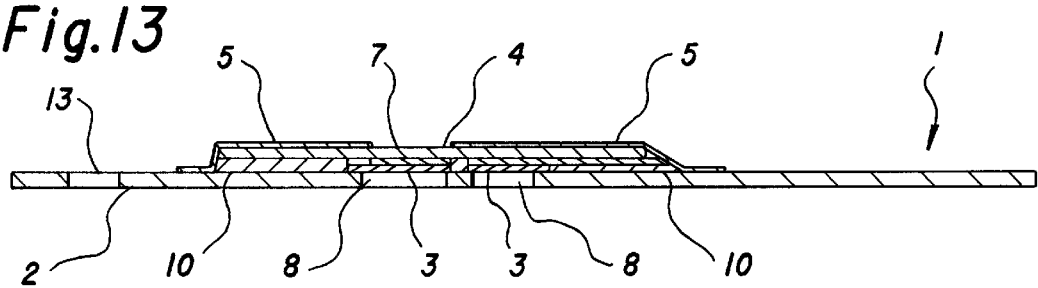
FIG. 13 shows a cross-section along A—A through a diagnostic test carrier of FIG. 11 according to the invention.

A diagnostic test carrier (1) according to the invention is shown in FIGS. 11–13 in which two detection layers (3) are located above a perforation (8) comprising two holes. One detection layer (3) is located above each hole of the perforation (8). The sample application site (7) in this case is located only above one of the two detection layers (3). Thus sample liquid (12) first passes into the detection layer (3) located under the sample application site (7) before by means of capillary forces in the area of the network (4) under the right cover (5) excess liquid also passes into the right detection layer (3) which can be observed through the rectangular hole in the supporting foil (2). Such a test carrier is for example suitable for the determination of an analyte with two detection layers (3) of different sensitivity. Advantageously a less sensitive universal field is located directly under the sample application site and an additional highly sensitive field is located next to it. This test carrier enables a measurement with the universal field in the case of small sample volumes and an improved measurement with both fields in the case of large sample volumes.

The test carrier (1) according to FIGS. 14–16 has an extra large sample application site (7) over a detection layer (3) which carries two reaction zones (9) which are directly adjacent to one another. These two reaction zones are visible from the underside of the carrier layer (2) through the perforation (8) which in this case is only composed of a single rectangular hole. Sample liquid (12) which is applied centrally to the sample application site (7) penetrates through the network (4) into the detection layer (3) and reaches both reaction zones (9) simultaneously. Such a test carrier can for example be used to determine two different analytes from one sample.

Figure 17:
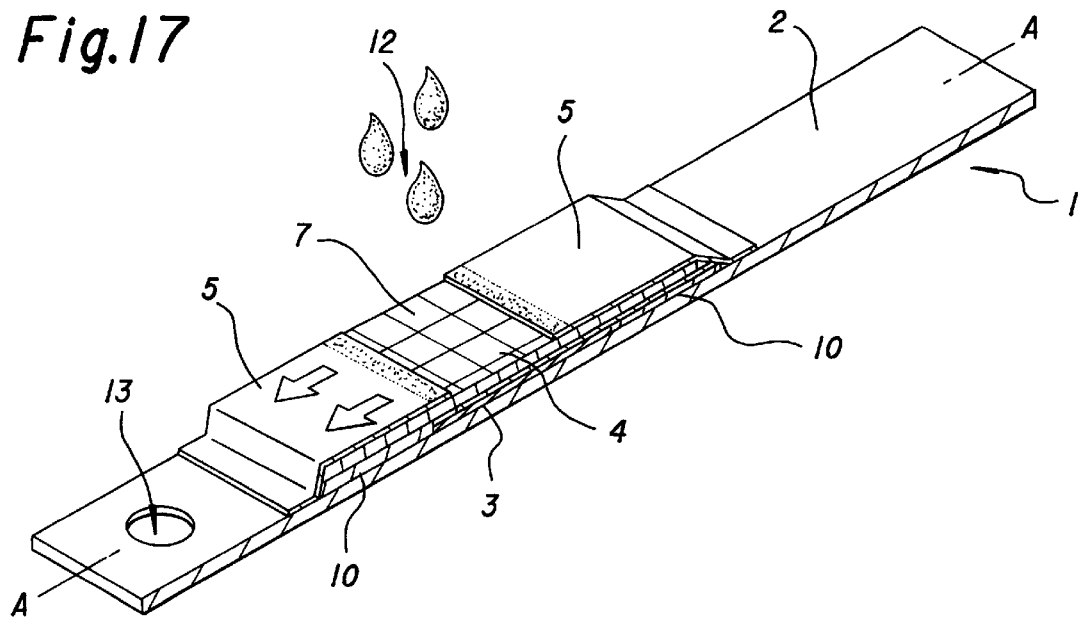
FIG. 17 shows a perspective view of a diagnostic test carrier according to the invention with a sample application site above one of the two reaction zones.
Figure 18:
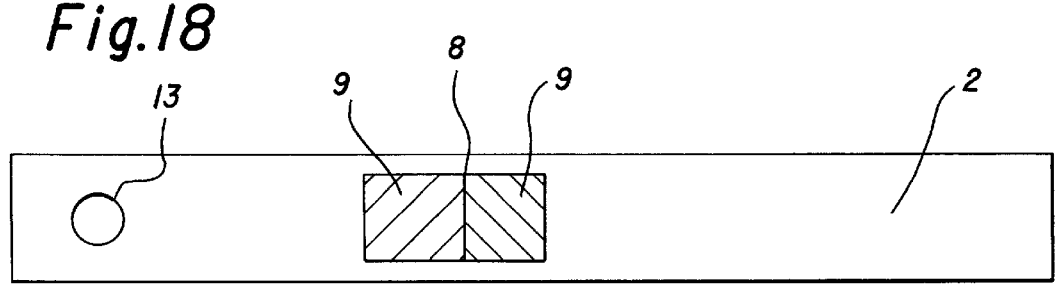
FIG. 18 shows a top view of the underside of a diagnostic test carrier of FIG. 17 according to the invention with a perforation comprising an extra large rectangular hole under a detection layer with two adjoining reaction zones.
Figure 19:
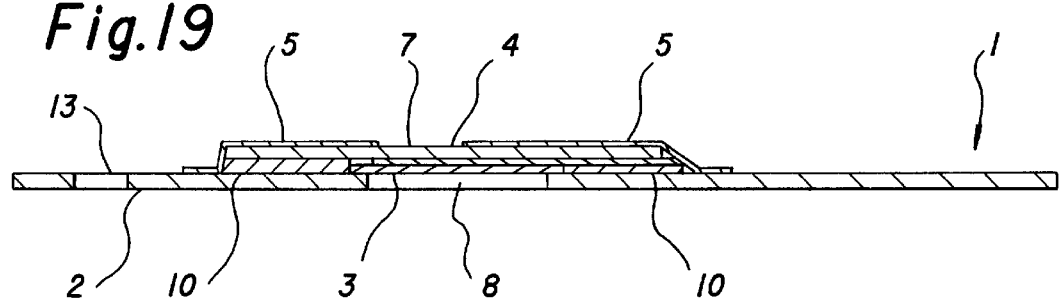
FIG. 19 shows a cross-section along A—A through a diagnostic test carrier of FIG. 17 according to the invention.

The test carrier (1) which is shown in FIGS. 17–19 corresponds essentially to the test carrier according to FIGS. 14–16. However, the sample application site (7) is only located above one of the two reaction zones (9). The right reaction zone (9) is protected from the direct application of sample liquid (12) by the right cover (5). Sample liquid (12) can only reach this via capillary forces within the area of the network (4) which is located under the right cover.

The invention is elucidated in more detail by the following examples.

EXAMPLE 1

Production of a Diagnostic Test Carrier According to the Invention for the Determination of Glucose A test carrier according to FIG. 1 is produced by the following working steps:

A 5 mm wide double-sided adhesive tape (polyester supporting and synthetic rubber adhesive) is mounted on a polyester supporting layer containing titanium dioxide. This composite is jointly punched with a 6 mm distance between the holes in order to produce the measuring holes. Afterwards the protective paper of the double-sided adhesive is removed.

A detection layer composed of 2 film layers is produced as follows:

A. The following components are added together in the following composition to a beaker as pure substances or in the form of stock solutions and admixed by stirring:

| | |
|---|---|
| Water: | 820.0 g |
| citric acid monohydrate: | 2.5 g |
| calcium chloride dihydrate | 0.5 g |
| sodium hydroxide: | 1.4 g |
| xanthan gum: | 3.4 g |
| tetraethylammonium chloride: | 2.0 g |
| N-octanoyl-N-methyl-glucamide: | 2.1 g |
| polyvinylpyrrolidone (MW 25000): | 3.5 g |
| Transpafill ® (sodium-aluminium silicate) | 62.1 g |
| polyvinylpropionate dispersion (50% by weight in water): | 60.8 g |
| bis-(2-hydroxyethyl)-(4-hydroximinocyclohexa-2,5-dienylidine)-ammonium chloride: | 1.2 g |
| 2,18-phosphoromolybdic acid hexasodium salt: | 16.1 g |
| pyrroloquinoline-quinone: | 32 mg |
| glucose dehydrogenase rec. from Acinetobacter calcoaceticus, EC 1.1.99.17: | 1.7 MU (2.4 g) |
| 1-hexanol: | 1.6 g |
| 1-methoxy-2-propanol: | 20.4 g |

The total composition is adjusted with NaOH to a pH of ca. 6 and then applied with an area weight of 89 g/qm onto a 125μ thick polycarbonate foil and dried.

B. The following components are added together in the following composition to a beaker as pure substances or in the form of stock solutions and admixed by stirring:

| | |
|---|---|
| water: | 579.7 g |
| sodium hydroxide: | 3.4 g |
| Gantrez ® (methyl vinyl ether maleic acid-copolymer): | 13.8 g |
| N-octanoyl-N-methyl-glucamide: | 3.6 g |
| tetraethylammonium chloride: | 9.7 g |
| polyvinylpyrrolidone (MW 25000): | 20.2 g |
| titanium dioxide: | 177.1 g |
| kieselguhr: | 55.3 g |
| polyvinylpropionate dispersion (50% by weight in water): | 70.6 g |
| 2,18-phosphoromolybdic acid hexasodium salt: | 44.3 g |
| potassium hexacyanoferrate (III): | 0.3 g |
| 1-hexanol: | 1.6 g |
| 1-methoxy-2-propanol: | 20.4 g |

The total composition is adjusted with NaOH to a pH of ca. 6 and then applied with an area weight of 104 g/qm onto a polycarbonate foil coated as described in A. and dried.

A 5 mm wide strip of the detection layer produced in this manner is fitted exactly and glued onto the supporting layer with its foil side on the punched double-sided adhesive tape.

Double-sided adhesive tapes as spacers (PVC support and natural rubber adhesive) are glued onto the support foil on both sides and directly adjoining the detection layer. In the present example one spacer is 6 mm and the other is 9 mm wide. Subsequently the protective foil of the two double-sided adhesive tapes is removed.

A yellow monofilament coarse meshed polyester fabric Scrynel PE 280 HC ("Zürcher Beuteltuchfabrik, Rüschlikon, Switzerland) impregnated with a wetting agent is placed on this compound structure and glued by pressing.

Two single-sided adhesive tapes (PVC support and natural rubber adhesive) are glued onto the yellow net as covers in such a way that the spacers are completely covered and that there is still at least a slight overlap with the reaction zone. This finishes the tape material.

The tape material is cut into 6 mm wide test carriers in such a way that the measuring hole is in the middle of the test carrier.

EXAMPLE 2
Volume Independency of the Test Carriers According to the Invention The test carriers from example 1 can be measured with a reflection photometer. The reflectance values which are a measure of the colour intensity can be converted into glucose concentrations when a calibration curve is available. If the term "relative reflectances" is used they refer to the reflectances on the dry test carrier.

A. Calibration curves are established by measuring a large number of venous blood samples with different glucose concentrations. The reflectance values and the glucose concentrations of these venous blood samples determined with a reference method can be used to set up a calibration curve.

Figure 20:
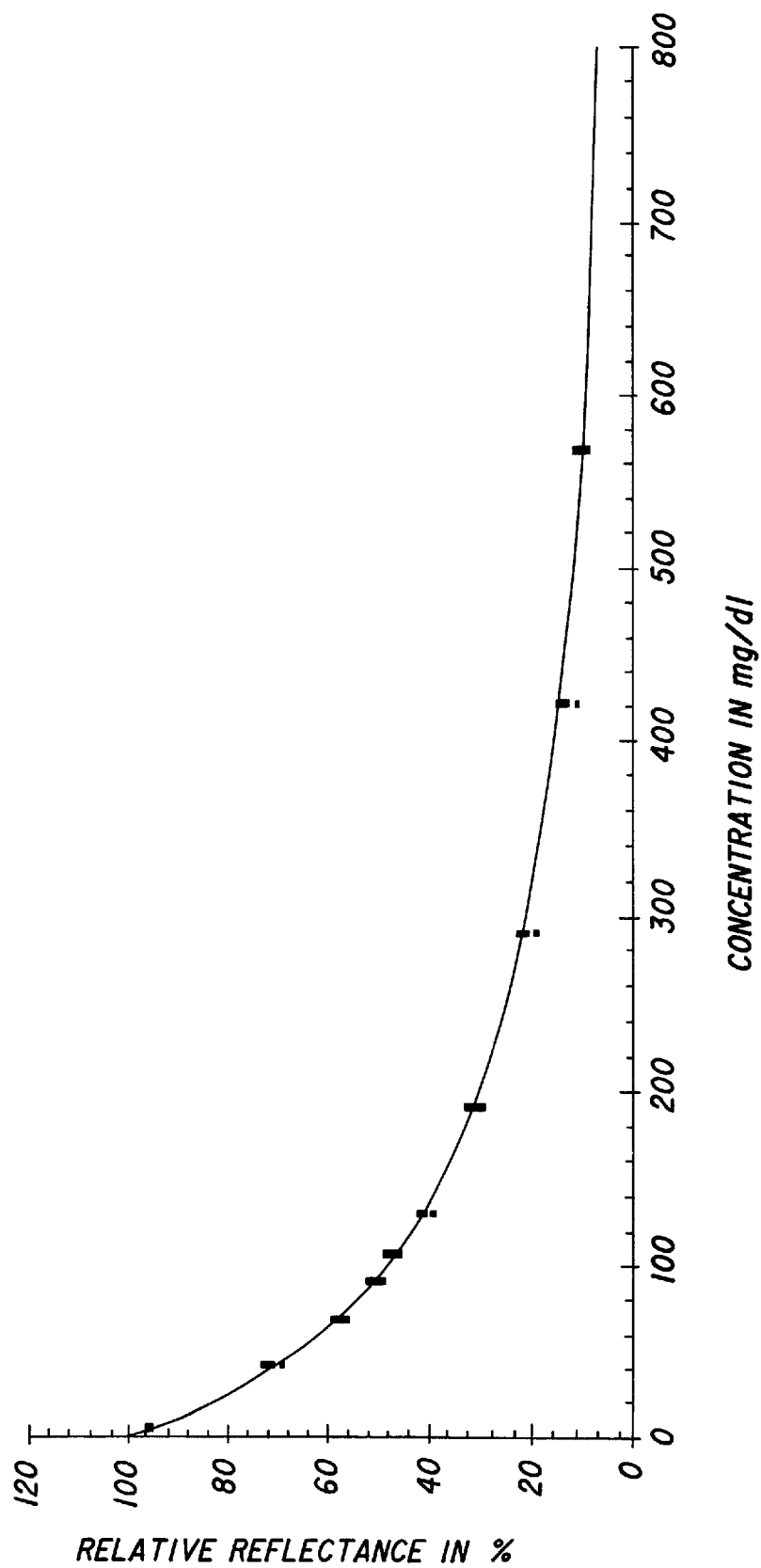
FIGS. 20, 21, 22 and 23 show calibration curves 1–4 which were generated as described in example 2.

In the calibration variant 1 10 $\mu$l venous blood was applied to test carriers according to example 1 and the reflectances were measured after 21 sec. The calibration curve 1 (FIG. 20) was determined by a regression calculation from the mean reflectances of 10 test carriers and the reference values of the blood samples.

Figure 21:
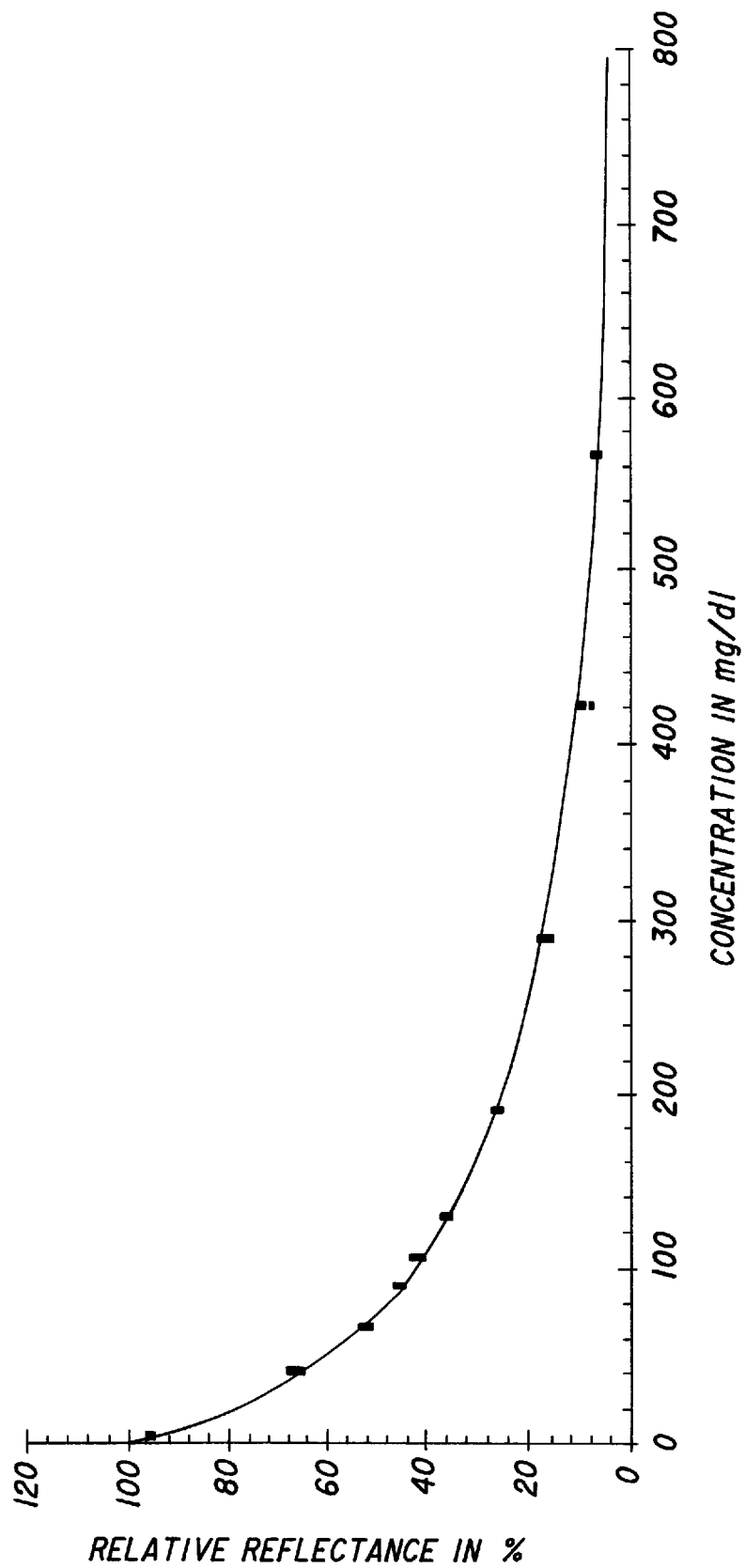

In the calibration variant 2 10 $\mu$l venous blood was also applied to test carriers according to example 1 and the reflectances were measured after 30 sec. The calibration curve 2 (FIG. 21) was determined by a regression calculation from the mean reflectances of 10 test carriers and the reference values of the blood samples.

Figure 22:
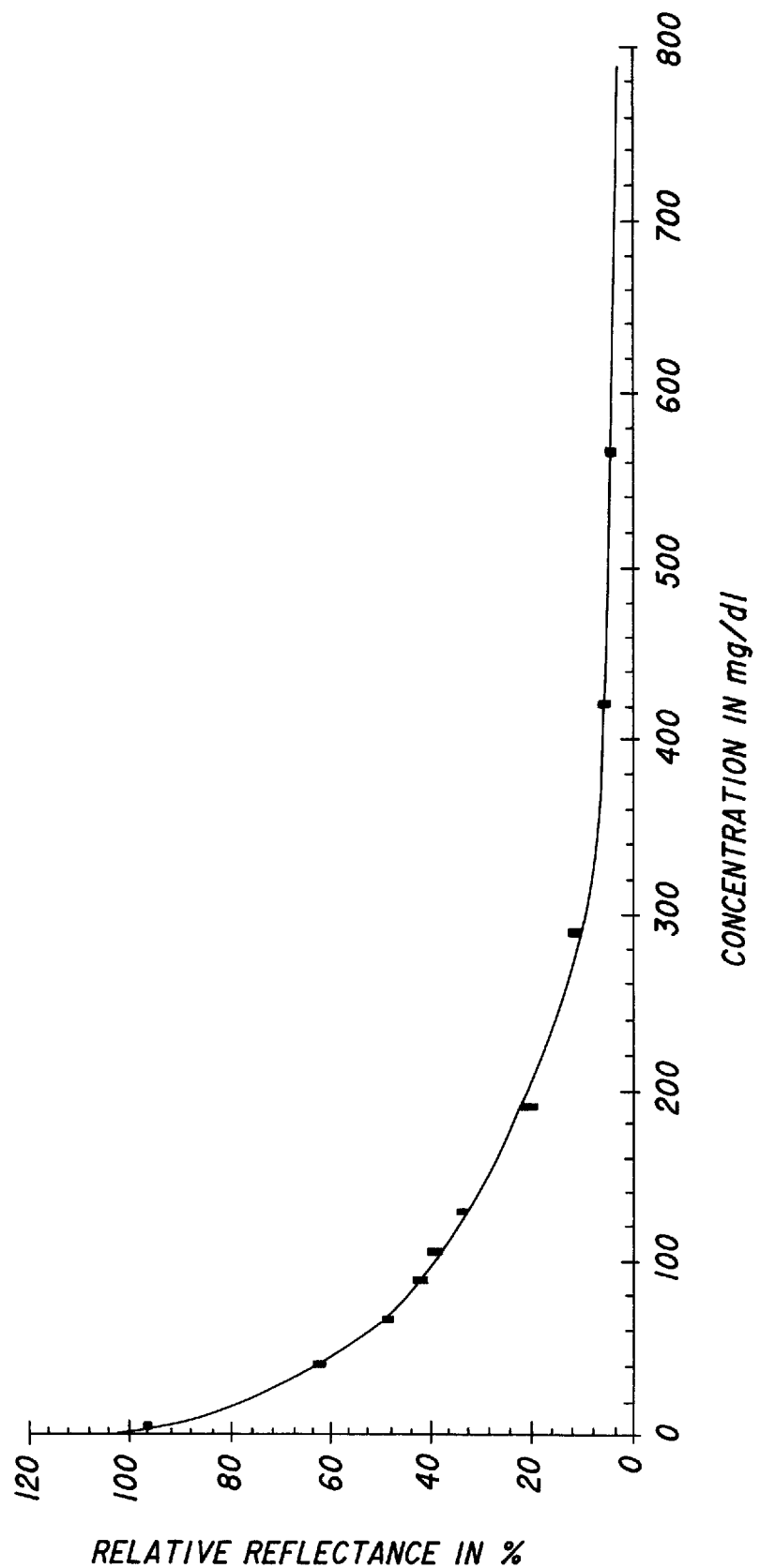

In the calibration variant 3 10 $\mu$l venous blood was also applied to test carriers according to example 1 and the reflectances were measured at intervals of 3 sec. As soon as the differences in reflectance were twice successively less than 0.3, the measurement was terminated and the reflectance value was used for the evaluation. The calibration curve 3 (FIG. 22) was determined by a regression calculation from the mean reflectances of 10 test carriers and the reference values of the blood samples.

Figure 23:
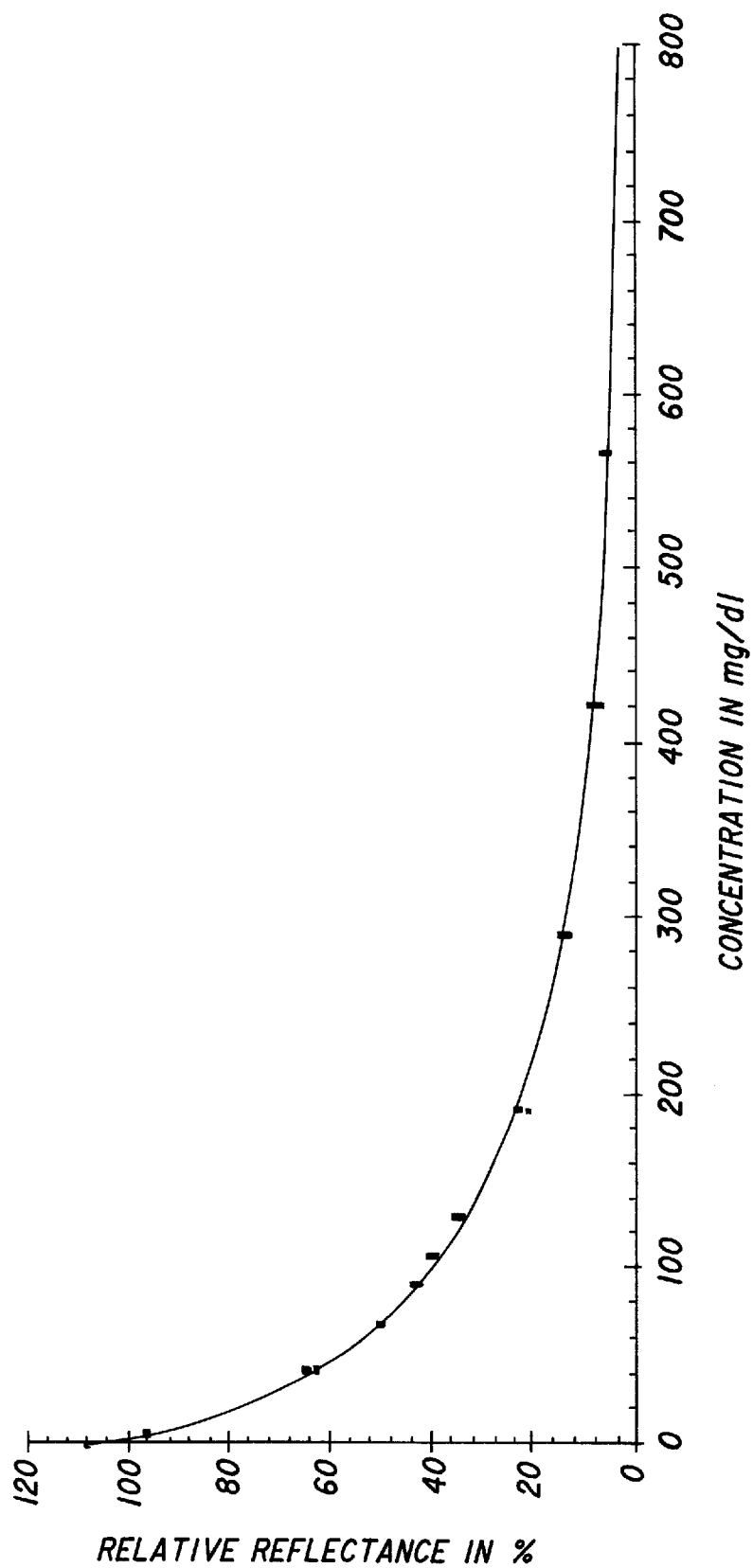

In the calibration variant 4 10 $\mu$l venous blood was also applied to test carriers according to example 1 and the reflectances were measured at intervals of 3 sec. As soon as the differences in reflectance were twice successively less than 0.9, the measurement was terminated and the reflectance value was used for the evaluation. The calibration curve 4 (FIG. 23) was determined by a regression calculation from the mean reflectances of 10 test carriers and the reference values of the blood samples.

B. In the case of measurement variant 1 different volumes of venous blood were applied to test carriers according to example 1 and the reflectances were measured after 21 sec. The individual reflectances were converted into glucose concentrations using the corresponding calibration curve according to FIG. 20. The deviation from accuracy was determined from the mean concentrations of 10 test carriers and the reference values of the blood samples and it is shown in Table 1.

In the case of the measurement variant 2 different volumes of venous blood were also applied to test carriers according to example 1 and the reflectances were measured after 30 sec. The individual reflectances were converted into glucose concentrations using the corresponding calibration curve according to FIG. 21. The deviation from accuracy was determined from the mean concentrations of 10 test carriers and the reference values of the blood samples and it is shown in Table 2.

In the case of the measurement variant 3 different volumes of venous blood were also applied to test carriers according to example 1 and the reflectances were measured at intervals of 3 sec. As soon as the differences in reflectance were twice successively less than 0.3, the measurement was terminated and the reflectance value was used for the evaluation. The individual reflectances were converted into glucose concentrations using the corresponding calibration curve according to FIG. 22. The deviation from accuracy was determined from the mean concentrations of 10 test carriers and the reference values of the blood samples and it is shown in Table 3.

In the case of the measurement variant 4 different volumes of venous blood were also applied to test carriers according to example 1 and the reflectances were measured at intervals of 3 sec. As soon as the differences in reflectance were twice successively less than 0.9, the measurement was terminated and the reflectance value was used for the evaluation. The individual reflectances were converted into glucose concentrations using the corresponding calibration curve according to FIG. 23. The deviation from accuracy was determined from the mean concentrations of 10 test carriers and the reference values of the blood samples and it is shown in Table 4.

TABLE 1

Volume tolerance of the test strip in measurement variant 1

| Sample volume | measured relative reflectance [%] | calculated concentration acc. to calibration curve 1 | deviation from the reference value in % |
|---|---|---|---|
| 3 μl | 42.8 | 117.5 | −0.5 |
| 5 μl | 42.9 | 117.1 | −0.8 |
| 8 μl | 42.6 | 118.5 | 0.4 |
| 10 μl | 41.8 | 122.1 | 3.4 |
| 20 μl | 41.9 | 121.6 | 3.0 |

TABLE 2

Volume tolerance of the test strip in measurement variant 2

| Sample volume | measured relative reflectance [%] | calculated concentration acc. to calibration curve 2 | deviation from the reference value in % |
|---|---|---|---|
| 3 μl | 37.4 | 117.5 | −0.5 |
| 5 μl | 37.6 | 117.0 | −0.9 |
| 8 μl | 37.4 | 117.7 | −0.3 |
| 10 μl | 37.2 | 118.6 | 0.4 |
| 20 μl | 37.0 | 119.4 | 1.1 |

TABLE 3

Volume tolerance of the test strip in measurement variant 3

| Sample volume | measured relative reflectance [%] | calculated concentration acc. to calibration curve 3 | deviation from the reference value in % |
|---|---|---|---|
| 3 μl | 33.4 | 120.2 | 1.5 |
| 5 μl | 34.0 | 117.7 | −0.6 |
| 8 μl | 33.9 | 118.0 | −0.3 |
| 10 μl | 34.1 | 117.0 | −1.2 |
| 20 μl | 33.8 | 118.5 | 0.1 |

TABLE 4

Volume tolerance of the test strip in measurement variant 4

| Sample volume | measured relative reflectance [%] | calculated concentration acc. to calibration curve 4 | deviation from the reference value in % |
|---|---|---|---|
| 3 μl | 35.2 | 119.2 | 0.8 |
| 5 μl | 35.3 | 118.7 | 0.3 |
| 8 μl | 35.6 | 117.3 | −0.8 |
| 10 μl | 35.6 | 117.4 | −0.8 |
| 20 μl | 35.4 | 118.0 | −0.3 |

C. As can be seen from the tables the test carriers according to the invention are largely independent of the volume.

What is claimed is:

1. A diagnostic test carrier for the determination of an analyte in a liquid sample, comprising a supporting layer;

at least one detection layer which contains reagents to determine an analyte in a liquid sample, and which detection layer is located on the supporting layer;

a network which covers the at least one detection layer and is larger than the at least one detection layer such that the network extends beyond the at least one detection layer to the supporting layer, to which supporting layer the network is attached, wherein the network is hydrophilic but essentially not capillary active; and a cover located over areas of the network which extend beyond each detection layer to define at least one sample application site which is not covered by the cover in the region of the network that covers the at least one detection layer;

wherein the network defines a capillary gap between the cover and the at least one detection layer, and the cover and the supporting layer, for the removal of excess liquid.

2. The diagnostic test carrier according to claim 1, wherein the supporting layer has a perforation, comprising at least one hole, over which at least one detection layer is located.

3. The diagnostic test carrier according to claim 1, wherein the liquid sample is a body fluid.

4. The diagnostic test carrier according to claim 3, wherein the liquid sample is a whole blood sample.

5. The diagnostic test carrier according to claim 1, wherein at least two detection layers are located next to one another on the supporting layer.

6. The diagnostic test carrier according to claim 5, wherein the perforation of the supporting layer comprises at least two holes over each of which a different detection layer is located.

7. The diagnostic test carrier according to claim 5, wherein each detection layer can detect separate analytes at the same time.

8. The diagnostic test carrier according to claim 1, wherein each detection layer contains at least two reaction zones, wherein each reaction zone has reagents capable of determining a different analyte.

9. The diagnostic test carrier according to claim 8, wherein the supporting layer contains a hole over which a detection layer containing the at least two reaction zones is located.

10. The diagnostic test carrier according to claim 6, wherein a sample application site is located over at least one detection layer.

11. The diagnostic test carrier according to claim 8, wherein a sample application site is located over at least one reaction zone.

12. The diagnostic test carrier according to claim 1, wherein the supporting layer is transparent.

13. The diagnostic test carrier according to claim 1, wherein the network is a monofilament fabric.

14. The diagnostic test carrier according to claim 1, wherein the network is attached to the supporting layer by means of an adhesive tape.

15. The diagnostic test carrier according to claim 1, wherein the cover and supporting layer are essentially impermeable to the liquid sample.

16. The diagnostic test carrier according to claim 1, wherein the network is a coarse-meshed monofilament fabric.

17. The diagnostic test carrier according to claim 1, wherein the at least one detection layer comprises at least one layer of material which is able to absorb the liquid together with the analyte to be determined contained therein.

18. The diagnostic test carrier according to claim 1, wherein the reagents for each of the at least one detection layers are impregnated in at least one layer of material.

19. The diagnostic test carrier according to claim 1, wherein the reagents for each of the at least one detection layers are coated on at least one layer of material.

20. The diagnostic test carrier according to claim 1, wherein each detection layer includes at least one layer which can separate plasma from whole blood.

21. The diagnostic test carrier according to claim 1, wherein the detection layer is a paper.

22. The diagnostic test carrier according to claim 1, wherein the detection layer is a porous plastic material.

23. The diagnostic test carrier according to claim 1, wherein the network is attached to the supporting layer beyond each detection layer by spacers which are about the same thickness as the detection layer.

24. A diagnostic test carrier for the determination of an analyte in a liquid sample, comprising a supporting layer;

at least one detection layer which contains reagents to determine an analyte in a liquid sample, and which detection layer is located on the supporting layer;

a network which covers the at least one detection layer and is larger than the at least one detection layer such that the network extends beyond each detection layer to the supporting layer, to which supporting layer the network is attached, wherein the network is hydrophilic but essentially not capillary active; and a cover located over areas of the network which extend beyond each detection layer to define at least one sample application site which is not covered by the cover in the region of the network that covers the at least one detection layer;

wherein the network defines a capillary gap between the cover and the detection layer, and between the cover and the supporting layer, for the removal of excess liquid; and wherein the detection layer comprises a transparent foil having a bottom foil side defining the detection side of the detection layer, and a top non-foil side, wherein a first film layer is applied to the top non-foil side and a second film layer is applied thereon, wherein the first film layer while in a wet state scatters light less than the second film layer scatters light.

25. The diagnostic test carrier according to claim 24, wherein the transparent foil is polycarbonate.

26. The diagnostic test carrier according to claim 24, wherein the first film layer has a swelling agent.

27. The diagnostic test carrier according to claim 24, wherein the second film layer has a swelling agent and at least one pigment that scatters light strongly.

28. The diagnostic test carrier according to claim 24, wherein the second film layer contains a pigment which has a refractive index of at least 2.5.

29. The diagnostic test carrier according to claim 24, wherein the first film layer contains no fillers.

30. The diagnostic test carrier according to claim 24, wherein the first film layer contains fillers whose refractive index is about the refractive index of water.

31. The diagnostic test carrier according to claim 24, wherein the first film layer has a pigment of sodium aluminum silicate.

32. The diagnostic test carrier according to claim 24, wherein the second film layer has a pigment of titanium dioxide.

33. The diagnostic test carrier according to claim 24, wherein the first film layer and the second film layer contain a non-haemolyzing wetting agent.

34. The diagnostic test carrier according to claim 24, wherein the thickness of the first film layer and the second film layer together in the dry state are a maximum of 0.20 mm.

35. The diagnostic test carrier according to claim 24, wherein the thickness of the first film layer and the second film layer together in the dry state are a maximum of 0.08 mm.

36. The diagnostic test carrier according to claim 24, wherein the second film layer is about two times to about five times thicker than the first film layer.

37. A method of determining an analyte in a liquid sample, using a diagnostic test carrier comprising a supporting layer, at least one detection layer containing at least one reagent, wherein the at least one detection layer is located on the supporting layer, a network which covers the at least one detection layer and is larger than the at least one detection layer such that the network extends beyond the at least one detection layer to the supporting layer, to which supporting layer the network is attached, and wherein the network is hydrophilic but essentially not capillary active, a cover located over areas of the network which extend beyond each detection layer to define at least one sample application site which is not covered by the cover in the region of the network that covers each detection layer, wherein the network defines a capillary gap between the cover and the detection layer, and between the cover and the supporting layer, for the removal of excess liquid, comprising applying the liquid sample at the at least one application site to the network, to pass the liquid sample through the network, and remove the excess sample by capillary action, wherein the liquid sample contacts at least one detection layer, to produce a detectable signal in the detection layer from the reaction of the sample with the reagents; and detecting the signal.

38. The method of determining an analyte in a liquid sample according to claim 37, wherein the detectable signal is a color change signal.

39. The method of determining an analyte in a liquid sample according to claim 37, wherein the liquid sample is a body fluid.

40. The method of determining an analyte in a liquid sample according to claim 39, wherein the liquid sample is blood.

* * * * *